United States Patent
Ota et al.

(10) Patent No.: US 7,273,906 B2
(45) Date of Patent: Sep. 25, 2007

(54) DIP-FORMING LATEX, DIP-FORMING COMPOSITION AND DIP-FORMED ARTICLE

(75) Inventors: Hisanori Ota, Tokyo (JP); Shunjin Aihara, Tokyo (JP); Kazumi Kodama, Tokyo (JP)

(73) Assignee: Zeon Corproation, Tokyo (JP)

( * ) Notice: Subject to any disclaimer, the term of this patent is extended or adjusted under 35 U.S.C. 154(b) by 254 days.

(21) Appl. No.: 10/505,734

(22) PCT Filed: Feb. 27, 2003

(86) PCT No.: PCT/JP03/02252

§ 371 (c)(1),
(2), (4) Date: Aug. 26, 2004

(87) PCT Pub. No.: WO03/072619

PCT Pub. Date: Sep. 4, 2003

(65) Prior Publication Data

US 2005/0154122 A1  Jul. 14, 2005

(30) Foreign Application Priority Data

Feb. 28, 2002 (JP) ............................. 2002-053491
Mar. 19, 2002 (JP) ............................. 2002-075326
May 17, 2002 (JP) ............................. 2002-142621

(51) Int. Cl.
*C08L 9/04* (2006.01)
*C08L 33/02* (2006.01)
*C08L 33/18* (2006.01)

(52) U.S. Cl. ...................... 524/571; 524/556; 524/565; 524/821; 524/832

(58) Field of Classification Search ................ 524/556, 524/565, 571, 821, 832
See application file for complete search history.

(56) References Cited

U.S. PATENT DOCUMENTS

| | | | |
|---|---|---|---|
| 4,102,844 A * | 7/1978 | Schwinum et al. | 524/745 |
| 5,014,362 A * | 5/1991 | Tillotson et al. | 2/168 |
| 5,286,783 A | 2/1994 | Hisaki et al. | |
| 5,369,166 A * | 11/1994 | Ozawa et al. | 524/560 |
| 5,910,533 A * | 6/1999 | Ghosal et al. | 524/560 |
| 6,031,042 A * | 2/2000 | Lipinski | 524/566 |
| 6,187,857 B1 * | 2/2001 | Ozawa et al. | 524/565 |
| 6,566,435 B1 * | 5/2003 | Teoh et al. | 524/432 |
| 6,844,385 B1 * | 1/2005 | Hagiwara et al. | 524/323 |

FOREIGN PATENT DOCUMENTS

EP  0 778 288 A  6/1997

* cited by examiner

*Primary Examiner*—Helen L Pezzuto
(74) *Attorney, Agent, or Firm*—Birch, Stewart, Kolasch & Birch, LLP

(57) ABSTRACT

A dip-forming latex obtained by copolymerization of (a) 50-89.5 weight parts of a conjugated diene monomer, (b) 10-40 weight parts of an ethylenically unsaturated nitrile monomer, (c) 0.5-10 weight parts of an ethylenically unsaturated acid monomer and (d) 0-20 weight parts of other copolymerizable ethylenically unsaturated monomer (the total of these monomers is 100 weight parts), wherein the copolymerization is initiated with a monomer mixture comprising at least 80 wt. % of (a), at least 50 wt. % of (b), 10-90 wt. % of (c) and least 80 wt. % of (d), and thereafter, the remainders of monomers are added to a polymerization system to continue copolymerization. This latex gives a dip-formed article exhibiting good softness of touch, high tensile strength and good retention of close fittingness.

7 Claims, No Drawings

US 7,273,906 B2

DIP-FORMING LATEX, DIP-FORMING COMPOSITION AND DIP-FORMED ARTICLE

TECHNICAL FIELD

This invention relates to a dip-forming latex, a dip-forming composition, and a dip-formed article. More particularly, it relates to a dip-forming latex made by copolymerization of a conjugated diene monomer, an ethylenically unsaturated monomer and an ethylenically unsaturated acid monomer; a dip-forming composition comprising the dip-forming latex; and a dip-formed article made by dip-forming the dip-forming composition.

The dip-formed article exhibits good softness of touch, high tensile strength and preferably good retention of tight fitness, and is useful as, for example, gloves.

BACKGROUND ART

Rubber gloves are widely used for household uses, industrial uses in, for example, food industry and electronic part industry, and surgical and other medical uses. It is generally required for rubber gloves that (1) they have good softness of touch and are well-fitting and comfortable to wear, namely, they are capable of being easily stretched in conformity with movement of fingers so that fatigue does not itself felt even when they are worn for long hours, (2) they are not easily broken, namely, they have a high tensile strength, and (3) they exhibit good retention of close fittingness, namely, they are not easily slackened nor crumpled when fingers are moved, and they keep a well-fitted state for a long time.

Rubber gloves made by dip-forming natural rubber latex have widely been used, but, allergies to natural rubber sometimes cause rashes or itching due to protein contained in a slight amount in natural rubber.

Rubber gloves made by dip-forming a synthetic rubber latex, for example, an acrylonitrile-butadiene copolymer latex, are known. Allergy does not develop to rubber gloves made from an acrylonitrile-butadiene copolymer latex, but these gloves exhibit poor balance between the softness of touch or comfortable fittingness, and the tensile strength.

For example, U.S. Pat. No. 5,014,362 discloses gloves dip-formed from a composition comprising a carboxyl-modified acrylonitrile-butadiene copolymer latex having incorporated therein minor amounts of zinc oxide, sulfur and a vulcanization accelerator, which are characterized as exhibiting a tensile stress retention of almost zero % as expressed by the formula of (A/B)×100 wherein B is tensile stress as measured immediately after 100% elongation and A is tensile stress as measured when 6 minutes elapses from the measurement of B. These gloves are easily stretched, well-fitting and comfortable to wear, but their retention of close fittingness is poor.

International publication WO 97/48765 discloses gloves dip-formed from a composition comprising a carboxyl-modified acrylonitrile-butadiene copolymer latex, ammonium casein, sulfur and a vulcanization accelerator, and not containing zinc oxide. These gloves have high tensile strength, but they are not easily stretched and do not exhibit comfortable fittingness, and their retention of close fittingness is poor.

U.S. Pat. No. 5,910,533 discloses a dip-formed article made from a copolymer latex prepared by copolymerization of 80 to 99% by weight of a conjugated diene monomer, 0 to 10% by weight of an unsaturated acid monomer and 0 to 20% by weight of other unsaturated monomers such as acrylonitrile and methyl methacrylate. As a specific example of the copolymer latex, a copolymer latex comprised of 87 weight parts of butadiene, 10 parts of acrylonitrile and 3 weight parts of methacrylic acid is mentioned. Gloves made from this copolymer latex can easily be stretched, have good softness of touch and are comfortable to wear, but the tensile strength is low and they are liable to be broken during wearing.

International publication WO 00/21451 discloses gloves made by dip-forming a composition comprising an acrylonitrile-butadiene copolymer latex containing a specific amount of a carboxyl group, an extremely slight amount of zinc oxide, sulfur and a vulcanization accelerator, which are characterized as exhibiting a tensile stress retention in a range of 50 to 70%. These gloves exhibit good retention of close fittingness, but the balance between the softness of touch or comfortable fittingness and the tensile strength is occasionally poor.

DISCLOSURE OF THE INVENTION

In view of the foregoing, an object of the present invention is to provide a dip-formed article having good softness of touch and comfortable fittingness, and high tensile strength.

Another object of the present invention is to provide a dip-formed article having good softness of touch, comfortable fittingness, high tensile strength, and an enhanced retention of close fittingness.

Other objects of the present invention are to provide a dip-forming composition giving the above-mentioned dip-formed article; and a dip-forming latex used for the dip-forming composition.

In one aspect of the present invention, there is provided a dip-forming latex obtained by copolymerization of 50 to 89.5 parts by weight of a conjugated diene monomer, 10 to 40 parts by weight of an ethylenically unsaturated nitrile monomer, 0.5 to 10 parts by weight of an ethylenically unsaturated acid monomer and 0 to 20 parts by weight of other copolymerizable ethylenically unsaturated monomer, provided that the total of these monomers is 100 parts by weight, wherein said copolymerization is initiated with a monomer mixture comprising at least 80% by weight of the amount of conjugated diene monomer used, at least 50% by weight of the amount of ethylenically unsaturated nitrile monomer used, 10 to 90% by weight of the amount of ethylenically unsaturated acid monomer used and at least 80% by weight of the amount of other copolymerizable ethylenically unsaturated monomer used, and thereafter, the remainders of monomers are added to a polymerization system to continue copolymerization.

In another aspect of the present invention, there is provided a dip-forming composition comprising the above-mentioned dip-forming latex.

In another aspect of the present invention, there is provided a dip-formed article made by dip-forming the above-mentioned dip-forming composition.

BEST MODE FOR CARRYING OUT THE INVENTION

The dip-forming latex of the present invention is obtained by copolymerization of 50 to 89.5 parts by weight of a conjugated diene monomer, 10 to 40 parts by weight of an ethylenically unsaturated nitrile monomer, 0.5 to 10 parts by weight of an ethylenically unsaturated acid monomer and 0 to 20 parts by weight of other copolymerizable ethylenically unsaturated monomer, provided that the total of these monomers is 100 parts by weight. The copolymerization is carried out in a manner such that the copolymerization is initiated with a monomer mixture comprising at least 80% by weight of the amount of conjugated diene monomer used, at least 50% by weight of the amount of ethylenically unsaturated nitrile monomer used, 10 to 90% by weight of the amount of ethylenically unsaturated acid monomer used and at least 80% by weight of the amount of other copolymerizable ethylenically unsaturated monomer used, and thereafter, the remainders of monomers are added to a polymerization system to continue copolymerization.

In a first preferable embodiment of the dip-forming latex, the dip-forming latex is obtained by a copolymerization procedure such that the copolymerization is initiated with a monomer mixture comprising at least 80% by weight of the amount of conjugated diene monomer used, at least 80% by weight of the amount of ethylenically unsaturated nitrile monomer used, 10 to 90% by weight of the amount of ethylenically unsaturated acid monomer used and at least 80% by weight of the amount of other copolymerizable ethylenically unsaturated monomer used, and thereafter, the remainders of monomers are added to a polymerization system to continue copolymerization. Preferably, after the copolymerization of the monomer mixture is initiated, the remainder of ethylenically unsaturated acid monomer is added while the polymerization conversion of the total monomers is within a range of 5 to 90%, and the remainders of conjugated diene monomer, ethylenically unsaturated nitrile monomer and other copolymerizable ethylenically unsaturated monomer are added at any time before the termination of copolymerization. This first embodiment of the dip-forming latex is hereinafter referred to "first dip-forming latex" when appropriate. The first dip-forming latex gives a dip-formed article having good softness of touch, comfortable fittingness, and high tensile strength.

In a second preferable embodiment of the dip-forming latex, the dip-forming latex is obtained by a copolymerization procedure such that the copolymerization is initiated with a monomer mixture comprising at least 80% by weight of the amount of conjugated diene monomer used, 50 to 90% by weight of the amount of ethylenically unsaturated nitrile monomer used, 40 to 90% by weight of the amount of ethylenically unsaturated acid monomer used and at least 80% by weight of the amount of other copolymerizable ethylenically unsaturated monomer used, and thereafter, the remainders of ethylenically unsaturated nitrile monomer and ethylenically unsaturated acid monomer are added while the polymerization conversion of the total monomers is within a range of 5 to 95%, and the remainders of conjugated diene monomer and other copolymerizable ethylenically unsaturated monomer are added at any time before the termination of copolymerization. This second embodiment of the dip-forming latex is hereinafter referred to "second dip-forming latex" when appropriate. The second dip-forming latex gives a dip-formed article having an enhanced retention of close fittingness, as well as good softness of touch, comfortable fittingness and high tensile strength.

By the term "the polymerization conversion of the total monomers added" as used in this specification, we mean the ratio (A/B) of the amount (A) of total monomers which have been converted to a copolymer to the amount (B) of total monomers which have been added to a polymerization system. For example, in the case when, after the initiation of polymerization of an initially charged monomer mixture, a first part of the remainder of a monomer is added to a polymerization system, the above-mentioned term as of the addition of the first part of monomer means the polymerization conversion of the monomers in the initially charged monomer mixture. In the case when, after the initiation of polymerization of an initially charged monomer mixture and further after addition of the first part of the remainder of a monomer, a second part of the remainder thereof is added to a polymerization system, the above-mentioned term as of the addition of the second part of monomer means the polymerization conversion of the sum of the monomers in the initially charged monomer mixture and the first part of the remainder of monomer.

The amount (A) of total monomers which have been converted to a copolymer is determined, for example, by calculation thereof by deducting the amount of total unreacted monomers from the amount (B) of total monomers which have been added to a polymerization system.

The conjugated monomer includes, for example, 1,3-butadiene, isoprene, 2,3-dimethyl-1,3-butadiene, 2-ethyl-1,3-butadiene, 1,3-pentadiene and chloroprene. Of these, 1,3-butadiene and isoprene are preferable. 1,3-Butadiene is especially preferable. These conjugated diene monomers may be used either alone or as a combination of at least two thereof.

The amount of conjugated diene monomer is in the range of 50 to 89.5 parts by weight, preferably 55 to 84 parts by weight, more preferably 65 to 81 parts by weight, and especially preferably 70 to 80 parts by weight, based on 100 parts by weight of the total amount of monomers. If the amount of conjugated diene monomer is too small, the dip-formed article is not satisfactory in softness of touch and comfortable fittingness. In contrast, if the amount of conjugated diene monomer is too large, the dip-formed article has low tensile strength.

As specific examples of the ethylenically unsaturated nitrile monomer, there can be mentioned acrylonitrile, methacrylonitrile, fumaronitrile, α-chloroacrylonitrile and α-cyanoethylacrylonitrile. Of these, acrylonitrile and methacrylonitrile are preferable. Acrylonitrile is especially preferable. The ethylenically unsaturated nitrile monomer may be used either alone or as a combination of at least two thereof.

The amount of ethylenically unsaturated nitrile monomer is in the range of 10 to 40 parts by weight, preferably 15 to 36 parts by weight, more preferably 18 to 27 parts by weight, and especially preferably 18 to 24 parts by weight, based on 100 parts by weight of the total amount of monomers. If the amount of ethylenically unsaturated nitrile monomer is too small, the dip-formed article has low tensile strength. In contrast, if the amount of ethylenically unsaturated nitrile monomer is too large, the dip-formed article is not satisfactory in softness of touch and comfortable fittingness.

The ethylenically unsaturated acid monomer includes ethylenically unsaturated monomers having an acidic group such as a carboxyl group, a sulfonic acid group or an acid anhydride group. As specific examples of the ethylenically unsaturated acid monomer, there can be mentioned ethylenically unsaturated monocarboxylic acid monomers such as acrylic acid and methacrylic acid; ethylenically unsaturated polycarboxylic acid monomers such as itaconic acid, maleic acid and fumaric acid; ethylenically unsaturated polycarboxylic acid anhydride monomers such as maleic anhydride and citraconic anhydride; ethylenically unsaturated sulfonic acid monomers such as styrenesulfonic acid; and ethylenically unsaturated polycarboxylic acid partial ester monomers such as monobutyl fumarate, monobutyl maleate and mono-2-hydroxypropyl maleate. Of these, ethylenically unsaturated carboxylic acid monomers are preferable. Ethylenically unsaturated monocarboxylic acid monomers are more preferable. Methacrylic acid is especially preferable. These ethylenically unsaturated acid monomers may be used in the form of a salt such as an alkali metal salt or an ammonium salt. The ethylenically unsaturated acid monomers may be used either alone or as a combination of at least two thereof.

The amount of ethylenically unsaturated acid monomer is in the range of 0.5 to 10 parts by weight, preferably 1 to 9 parts by weight, more preferably 1 to 8 parts by weight, and especially preferably 2 to 6 parts by weight, based on 100 parts by weight of the total amount of monomers. If the amount of ethylenically unsaturated acid monomer is too small, the dip-formed article has low tensile strength. In contrast, if the amount of ethylenically unsaturated acid monomer is too large, the dip-formed article is not satisfactory in softness of touch, comfortable fittingness, and retention of close fittingness.

As specific examples of the other copolymerizable ethylenically unsaturated monomers which are optionally used, there can be mentioned vinyl aromatic monomers such as styrene, alkylstyrenes and vinyl naphthalene; fluoroalkyl vinyl ether monomers such as fluoroethyl vinyl ether; ethylenically unsaturated amide monomers such as acrylamide, N-methylolacrylamide, N,N-dimethylolacrylamide, N-methoxymethylacrylamide, N-propoxymethylacrylamide, methacrylamide, N-methylol-methacrylamide, N,N-dimethylolmethacrylamide, N-methoxymethylmethacrylamide and N-propoxymethyl-methacrylamide; ethylenically unsaturated carboxylic acid ester monomers such as methyl acrylate, ethyl acrylate, butyl acrylate, 2-ethylhexyl acrylate, trifluoroethyl acrylate, tetrafluropropyl acrylate, methoxymethyl acrylate, ethoxyethyl acrylate, methoxyethoxyethyl acrylate, cyanomethyl acrylate, 2-cyanoethyl acrylate, 1-cyanopropyl acrylalte, 2-ethyl-6-cyanohexyl acrylate, 3-cyanopropyl acrylate, hydroxyethyl acrylate, hydroxypropyl acrylate, glycidyl acrylate, dimethylaminoethyl acrylate, methyl methacrylate, ethyl methacrylate, butyl methacrylate, 2-ethylhexyl methacrylate, trifluoroethyl methacrylate, tetrafluoropropyl methacrylate, methoxymethyl methacrylate, ethoxyethyl methacrylate, methoxyethoxyethyl methacrylate, cyanomethyl methacrylate, 2-cyanoethyl methacrylate, 1-cyanopropyl methacrylate, 2-ethyl-6-cyanohexyl methacrylate, 3-cyanopropyl methacrylate, hydroxyethyl methacrylate, hydroxypropyl methacrylate, glycidyl methacrylate, dimethylaminoethyl methacrylate, dibutyl maleate, dibutyl fumarate and diethyl maleate; and crosslinking monomers such as divinylbenzene, polyethylene glycol diacrylate, polyethylene glycol dimethacrylate, polypropylene glycol diacrylate, polypropylene glycol dimethacrylate, trimethylolpropane triacrylate, trimethylolpropane trimethacrylate, pentaerithritol acrylate and pentaerithritol methacrylate. These optional ethylenically unsaturated monomers may be used either alone or as a combination of at least two thereof.

The amount of the optional ethylenically unsaturated monomer is not larger than 20 parts by weight, preferably not larger than 15 parts by weight, more preferably not larger than 10 parts by weight, and especially preferably not larger than 8 parts by weight, based on 100 parts by weight of the total amount of monomers. If the amount of the optional ethylenically unsaturated monomer is too large, the balance between the softness of touch and comfortable fittingness, and the tensile strength is poor.

The dip-forming latex of the present invention is obtained by copolymerization of the above-mentioned monomers, preferably by an emulsion copolymerization procedure.

In the copolymerization for the production of dip-forming latex, the time at which the monomers are added to a polymerization system is important. That is, the copolymerization is initiated with a monomer mixture comprising at least 80% by weight of the amount of conjugated diene monomer used, at least 50% by weight of the amount of ethylenically unsaturated nitrile monomer used, 10 to 90% by weight of the amount of ethylenically unsaturated acid monomer used and at least 80% by weight of the amount of other copolymerizable ethylenically unsaturated monomer used, and thereafter, the remainders of monomers are added to a polymerization system to continue copolymerization.

For the production of the above-mentioned first dip-forming latex, the copolymerization is initiated with a monomer mixture comprising at least 80% by weight of the amount of conjugated diene monomer used, at least 80% by weight of the amount of ethylenically unsaturated nitrile monomer used, 10 to 90% by weight of the amount of ethylenically unsaturated acid monomer used and at least 80% by weight of the amount of other copolymerizable ethylenically unsaturated monomer used, and thereafter, the remainders of monomers are added to a polymerization system to continue copolymerization. Preferably, after the copolymerization of the monomer mixture is initiated, the remainder of ethylenically unsaturated acid monomer is added while the polymerization conversion of the total monomers added is within a range of 5 to 90%, and the remainders of conjugated diene monomer, ethylenically unsaturated nitrile monomer and other copolymerizable ethylenically unsaturated monomer are added at any time before the termination of copolymerization.

For the production of the above-mentioned second dip-forming latex, the copolymerization is initiated with a monomer mixture comprising at least 80% by weight of the amount of conjugated diene monomer used, 50 to 90% by weight of the amount of ethylenically unsaturated nitrile monomer used, 40 to 90% by weight of the amount of ethylenically unsaturated acid monomer used and at least 80% by weight of the amount of other copolymerizable ethylenically unsaturated monomer used, and thereafter, the remainders of ethylenically unsaturated nitrile monomer and ethylenically unsaturated acid monomer are added while the polymerization conversion of the total monomers added is within a range of 5 to 95%, and the remainders of conjugated diene monomer and other copolymerizable ethylenically unsaturated monomer are added at any time before the termination of copolymerization.

The ethylenically unsaturated nitrile monomer is initially added in a polymerization vessel in an amount of at least 50% by weight of its total amount used for polymerization, and, after the initiation of polymerization, the remainder thereof is added to continue copolymerization.

More specifically, for the production of the first dip-forming latex, the ethylenically unsaturated nitrile monomer is initially added in a polymerization vessel preferably in an amount of at least 80% by weight, more preferably at least 90% and especially preferably 100% of its total amount used for polymerization, and, after the initiation of polymerization, the remainder thereof is added to continue copolymerization.

For the production of the second dip-forming latex, the ethylenically unsaturated nitrile monomer is initially added in a polymerization vessel preferably in an amount of 50 to 90% by weight, more preferably 55 to 85% by weight and especially preferably 60 to 85% by weight of its total amount used for polymerization. If the amount of ethylenically unsaturated nitrile monomer initially added in a polymerization vessel is too small, the dip-formed article has low tensile strength. In contrast, if the amount of ethylenically unsaturated nitrile monomer initially added is too large, the balance among the softness of touch, comfortable fittingness, tensile strength and retention of close fittingness tends to be poor.

After the initiation of polymerization for the production of the second dip-forming latex, the remainder of ethylenically unsaturated nitrile monomer is added while the polymerization conversion of the total monomers added is preferably within a range of 5 to 95%, more preferably 10 to 90% by weight and especially preferably 20 to 90% by weight. After the initiation of polymerization, if the remainder of ethylenically unsaturated nitrile monomer is added while the polymerization conversion of the total monomers added is too small, the dip-formed article tends to have poor softness of touch, poor fittingness and low tensile strength. In contrast, if the remainder of ethylenically unsaturated nitrile monomer is added while the polymerization conversion of the total monomers added is too large, the dip-formed article tends to have low tensile strength. The remainder of ethylenically unsaturated nitrile monomer is added preferably while the polymerization conversion of the ethylenically unsaturated nitrile monomer added is in the range of 40 to 95% by weight, more preferably 45 to 92% by weight and especially preferably 45 to 85% by weight for enhancement of tensile strength.

After the initiation of polymerization, the remainder of ethylenically unsaturated nitrile monomer is added preferably at two or more times. In this case, the amount of ethylenically unsaturated nitrile monomer added in each time is preferably equal to each other for more enhancement of balance between the softness of touch and comfortable fittingness, and the tensile strength. The number of times for the addition of ethylenically unsaturated nitrile monomer is not particularly limited, and may be infinite. That is, the remainder of ethylenically unsaturated nitrile monomer can be continuously added.

The ethylenically unsaturated acid monomer is initially added in a polymerization vessel in an amount of 10 to 90% by weight of its total amount used for polymerization, and, after the initiation of polymerization, the remainder thereof is added to continue copolymerization.

More specifically, for the production of the first dip-forming latex, the ethylenically unsaturated acid monomer is initially added in a polymerization vessel in an amount of 10 to 90% by weight, preferably 30 to 85% by weight and more preferably 50 to 80% by weight of its total amount used for polymerization, and, after the initiation of polymerization, the remainder thereof is added to continue copolymerization. If the amount of ethylenically unsaturated acid monomer initially added is too small, the dip-formed article has low tensile strength. In contrast, if the amount thereof initially added is too large, the dip-formed article is not satisfactory in softness of touch, comfortable fittingness and tensile strength.

After the initiation of polymerization for the production of the first dip-forming latex, the remainder of ethylenically unsaturated acid monomer is added while the polymerization conversion of the total monomers added is preferably within a range of 5 to 90%, more preferably 20 to 80% by weight and especially preferably 40 to 80% by weight. When the remainder of ethylenically unsaturated monomer is added while the polymerization conversion of the total monomers added is within this range, the dip-formed article has well balanced softness of touch, comfortable fittingness and tensile strength. The remainder of ethylenically unsaturated acid monomer may be added either in one lot, or in two or more lots. It can also be added in a continuous manner. The addition in one lot is preferable.

For the production of the second dip-forming latex, the ethylenically unsaturated acid monomer is initially added in a polymerization vessel in an amount of 40 to 90% by weight, preferably 50 to 85% by weight and more preferably 60 to 80% by weight of its total amount used for polymerization. If the amount of ethylenically unsaturated acid monomer initially added in a polymerization vessel is too small, the dip-formed article has poor tensile strength and poor retention of tight fitness. In contrast, if the amount of ethylenically unsaturated acid monomer initially added is too large, the dip-formed article is not satisfactory in softness of touch, comfortable fittingness and tensile strength.

After the initiation of polymerization for the production of the second dip-forming latex, the remainder of ethylenically unsaturated acid monomer is added while the polymerization conversion of the total monomers added is within a range of 5 to 95% by weight, preferably 10 to 90% by weight, more preferably 20 to 80% by weight and especially preferably 40 to 70% by weight. If the remainder of ethylenically unsaturated acid monomer is added while the polymerization conversion of the total monomers added is within this range, the dip-formed article has well-balanced and good softness of touch, comfortable fittingness and tensile strength. The remainder of ethylenically unsaturated acid monomer may be added either in one lot, or in two or more lots. It can also be added in a continuous manner. The addition in one lot is preferable.

The conjugated diene monomer is initially added in a polymerization vessel in an amount of at least 80% by weight, preferably at least 90% by weight of its total amount used for polymerization, and, after the initiation of polymerization, the remainder thereof is added to continue copolymerization. Preferably, the entire amount of conjugated diene monomer used for polymerization is initially added before the initiation of polymerization.

The optional other copolymerizable ethylenically unsaturated monomer is initially added in a polymerization vessel in an amount of at least 80% by weight, preferably at least 90% by weight of its total amount used for polymerization, and, after the initiation of polymerization, the remainder thereof is added to continue copolymerization. Preferably, the entire amount of the monomer used for polymerization is initially added before the initiation of polymerization.

The procedures for copolymerization may be conventional provided that the time at which the monomers are added to a polymerization system is satisfied with the above requirements. For example, in the case of an emulsion polymerization, a monomer mixture is polymerized by using a polymerization initiator in the presence of water and an emulsifier, and, when the polymerization conversion reaches a predetermined value, a polymerization stopper is added to terminate polymerization.

The emulsifier used for emulsion copolymerization is not particularly limited, and, as specific examples thereof, there can be mentioned nonionic emulsifiers such as polyoxyethylene alkyl ethers, polyoxyethylene alkyl phenol ethers, polyoxyethylene alkyl esters and polyoxyethylene sorbitan alkyl esters; anionic emulsifiers such as salts of fatty acids, for example, myristic acid, palmitic acid, oleic acid and linolenic acid, alkylbenzenesulfonic acid salts, for example, sodium dodecylbenzenesulfonate, and higher alcohol sulfuric acid ester salts and alkylsulfosuccinic acid salts; cationic emulsifiers such as alkyltrimethylammonium chloride, dialkylammonium chloride and benzylammonium chloride;

and copolymerizable emulsifiers such as sulfoesters of α,β-unsaturated carboxylic acids, sulfate esters of α,β-unsaturated carboxylic acids and sulfoalkyl aryl ethers. Of these, anionic emulsifiers are preferable. These emulsifiers may be used either alone or as a combination of at least two thereof. The amount of emulsifier is in the range of 0.1 to 10 parts by weight based on 100 parts by weight of the total monomers added.

The amount of water used for emulsion copolymerization is in the range of 80 to 500 parts by weight, preferably 100 to 300 parts by weight, based on 100 parts by weight of the total monomers added.

The polymerization initiator used is not particularly limited, and, as specific examples thereof, there can be mentioned inorganic peroxides such as sodium persulfate, potassium persulfate, ammonium persulfate, potassium perphosphate and hydrogen peroxide; organic peroxides such as diisopropylbenzene hydroperoxide, cumene hydroperoxide, tert-butyl hydroperoxide, 1,1,3,3-tetramethylbutyl hydroperoxide, 2,5-dimethylhexane-2,5-dihydroperoxide, di-tert-butyl hydroperoxide, di-α-cumyl peroxide, acetyl peroxide, isobutyryl peroxide and benzoyl peroxide; and azo compounds such as azobisisobutyronitrile, azobis-2,4-dimethylvaleronitrile and methyl azobisisobutyrate. These polymerization initiators may be used either alone or as a combination of at least two thereof. Peroxide polymerization initiators are preferable because a latex can be stably produced and a dip-formed article having enhanced softness of touch and high tensile strength can be obtained from the latex. The amount of polymerization initiator is preferably in the range of 0.01 to 1.0 part by weight based on 100 parts by weight of the total monomers added.

The peroxide polymerization initiator can be used in combination with a reducing agent, as a redox polymerization initiator. The reducing agent used is not particularly limited and includes, for example, compounds containing a metal ion in a reduced state such as ferrous sulfate and cuprous naphthenate; sulfonic acid compounds such as sodium methanesulfonic acid; and amine compounds such as dimethylaniline. These reducing agents may be used either alone or in combination. The amount of reducing agent is preferably in the range of 0.03 to 10 parts by weight based on 1 part by weight of peroxide.

As a polymerization stopper, there can be used, for example, hydroxylamine, hydroxylamine sulfate salt, diethyl hydroxylamine, hydroxylaminesulfonic acid and its alkali metal salts; sodium dimethyldithiocarbamate, hydroquinone derivatives and catechol derivatives; and aromatic hydroxydithiocarboxylic acids such as hydroxydimethylbenzenethiocarboxylic acid, hydroxydiethylbenzene-thiocarboxylic acid and hydroxydibutylbenzenethiocarboxylic acid, and alkali metal salts thereof. The amount of polymerization stopper is not particularly limited, but is usually in the range of 0.1 to 2 parts by weight based on 100 parts by weight of the total monomers added.

Polymerization auxiliaries can be used for emulsion copolymerization according to the need, which include, for example, a molecular weight modifier, a particle size modifier, a chelating agent and an oxygen scavenger.

The polymerization temperature is not particularly limited, but is usually in the range of 0 to 95° C., preferably 5 to 70° C.

The polymerization conversion at which the polymerization reaction is terminated is preferably at least 90%, more preferably at least 93%.

After the polymerization reaction is terminated, unreacted monomers are removed from a polymerization mixture and the solid content and pH value thereof are adjusted according to the need to give a desired copolymer latex.

Additives such as an antioxidant, a preservative, an antifungus agent and a dispersant can be incorporated in the thus-obtained latex according to the need.

The copolymer latex preferably has a number average particle diameter in the range of 60 to 300 nm, more preferably 80 to 150 nm. The particle diameter can be adjusted to a desired value by varying the amounts of an emulsifier and polymerization initiator.

The dip-forming composition of the present invention comprises the above-mentioned dip-forming latex.

Preferably a vulcanizing agent and a vulcanization accelerator are incorporated in the dip-forming composition of the present invention. If desired, zinc oxide can be further incorporated in the dip-forming composition.

As the vulcanizing agent, those which are conventionally used in dip-forming are mentioned. As specific examples thereof, there can be mentioned sulfur such as powdery sulfur, flower of sulfur, precipitated sulfur, colloidal sulfur, surface-treated sulfur and insoluble sulfur; and polyamines such as hexamethylenediamine, triethylenetetramine and tetraethylenepentamine. Of these, sulfur is preferable.

The amount of vulcanizing agent is preferably in the range of 0.5 to 10 parts by weight, more preferably 2 to 5 parts by weight and especially preferably 3.5 to 4.5 parts by weight based on 100 parts by weight of the solid content of latex.

As the vulcanization accelerator, those which are conventionally used in dip-forming are mentioned. As specific examples thereof, there can be mentioned dithiocarbamic acids such as diethyldithiocarbamic acid, dibutyldithiocarbamic acid, di-2-ethylhexyldithiocarbamic acid, dicyclohexyldithio-carbamic acid, diphenyldithiocarbamic acid and dibenzyldithiocarbamic acid, and zinc salt thereof; and 2-mercaptobenzothiazole, zinc salt of 2-mercaptobenzothiazole, 2-mercaptothiazoline, dibenzothiazyldisulfide, 2-(2,4-dinitrophenylthio)benzothiazole, 2-(N,N-diethylthio-carbaylthio)benzothiazole, 2-(2,6-dimethyl-4-morpholinothio)benzothiazole, 2-(4'-morpholino-dithio)benzothiazole, 4-morphonylyl-2-benzothiazyl disulfide and 1,3-bis(2-benzothiazyl-mercaptomethyl)urea. Of these, zinc dibutyldithiocarbamate, 2-mercaptobenzothiazole and zinc salt of 2-mercaptobenzothiazole are preferable. These vulcanization accelerators may be used either alone or as a combination of at least two thereof.

The amount of vulcanizing accelerator is preferably in the range of 0.1 to 10 parts by weight, more preferably 0.5 to 5 parts by weight and especially preferably 1 to 3 parts by weight based on 100 parts by weight of the solid content of latex.

The amount of zinc oxide is preferably not larger than 5 parts by weight, more preferably not larger than 1 part by weight and especially preferably not larger than 0.5 part by weight based on 100 parts by weight of the solid content of latex.

Conventional ingredients such as a pH adjuster, a thickener, an antioxidant, a dispersant, a pigment, a filler and a softener may be incorporated in the dip-forming composition of the present invention, according to the need. Provided that the object of the present invention is achieved, other latex such as natural rubber latex or isoprene rubber latex can be incorporated with the dip-forming latex.

The dip-forming composition of the present invention has a solid content in the range of 20 to 40% by weight, preferably 25 to 35% by weight.

The dip-forming composition of the present invention has a pH value in the range of 8.5 to 12, preferably 9 to 11.

The dip-formed article of the present invention is made by dip-forming the above-mentioned dip-forming composition. A conventional dip-forming method can be adopted, which includes, for example, a direct dip-forming method, an anode cohesion dip-forming method, a Teague cohesion dip-forming method and a combination of these methods. Of these, an anode cohesion dip-forming method is preferable because a dip-formed article having a uniform thickness is easily obtained.

The anode cohesion dip-forming method is carried out by a process comprising the steps of dipping a dip-forming form in a solution of a coagulant to form a layer comprised of the coagulant solution on the form; and dipping the form having the coagulating solution layer thereon in a dip-forming composition to form a coagulated layer comprised of the dip-forming composition.

As specific examples of the coagulant, there can be mentioned metal halides such as barium chloride, calcium chloride, magnesium chloride, zinc chloride and aluminum chloride; nitric acid salts such as barium nitrate, calcium nitrate and zinc nitrate; acetic acid salts such as barium acetate, calcium acetate and zinc acetate; and sulfuric acid salts such as calcium sulfate, magnesium sulfate and aluminum sulfate. Of these, calcium chloride and calcium nitrate are preferable.

The coagulant is usually used as a solution in water, an alcohol or a mixture thereof. The concentration of coagulant in the solution is usually in the range of 5 to 70% by weight, preferably 20 to 50% by weight.

The coagulated layer of the dip-forming composition, formed on the surface of a dip-forming form is usually heat-treated to cure.

The form having formed thereon the coagulated dip-forming composition layer can be dipped in water, preferably warm water maintained at a temperature of 30 to 70° C., for 1 to 60 minutes to remove water-soluble impurities such as, for example, excessive emulsifier and coagulant, from the coagulated dip-forming composition layer. This water washing can be carried out either before or after the heat-treatment of the coagulated dip-forming composition layer, but, the water washing is preferably carried out before the heat-treatment because water-soluble impurities can be more effectively removed.

The water-washed coagulated composition layer is heat-treated usually at a temperature of 100 to 150° C. for 10 to 120 minutes to cure the coagulated composition layer. The heating can be carried out by an external heating method using infrared rays or heated air, or an internal heating method using high frequency. Of these, an external heating method using heated air is preferable.

The cured, coagulated dip-forming composition layer is released from the form to obtain a dip-formed article. The release can be carried out manually or by applying water pressure or compressed air.

After the release from the form, the dip-formed article can be further heat-treated at a temperature of 60 to 120° C. for 10 to 120 minutes.

The dip-formed article may have a surface-treated layer formed on the inner surface and/or the outer surface.

By using the dip-forming latex of the present invention, a dip-formed article having a tensile stress at 300% elongation of not larger than 2.5 MPa, a tensile strength of at least 15 MPa, preferably at least 20 MPa, and a tensile stress retention of at least 70%, preferably larger than 70%, as measured when 6 minutes elapses from the time of 100% elongation, can be easily obtained. Further, a dip-formed article having these characteristics and a swelling degree in methyl ethyl ketone (hereinafter abbreviated to "MEK" when appropriate) of not larger than 200%, preferably not larger than 180%, can also be obtained. The smaller the swelling degree in MEK, the more excellent the oil resistance.

EXAMPLES

The invention will now be described by the following examples wherein % and parts are by weight unless otherwise specified.

Polymerization conversion of acrylonitrile in a polymerization mixture and properties of a dip-formed article were evaluated by the following methods.

Polymerization Conversion of Acrylonitrile (AN) (%)

A part of a polymerization liquid was taken, and the content of unreacted acrylonitrile (AN) was measured. From the amount (a) of AN initially charged and the measured content (b) of unreacted AN, the ratio (%) ([(a−b)/a]×100) of the amount of AN (a−b) converted to a copolymer to the amount (a) of AN initially charged was calculated. In the case when, after initiation of polymerization of an initially charged monomer mixture and further after addition of a first part of the remainder of AN, a second part of the remainder of AN is added, the polymerization conversion of AN as of the addition of the second part thereof is calculated from the formula:

Polymerization conversion of AN (%)= [(a+a')−b]/(a+a')×100 where a: amount of AN in initially charged monomer mixture
a': amount of first part of the remainder of AN
b: amount of unreacted AN Tensile Stress at 300% Elongation (MPa)

A dumbbell specimen (Die-C) was punched out from a dip-formed article of a glove form, according to ASTM D412.

Tensile stress at 300% elongation was measured on the dumbbell specimen at a drawing rate of 500 mm/min by Tensilon tensile tester ("RTC-1225A" availavle from Orientec K.K.). The smaller the tensile stress at 300% elongation, the more excellent the softness of touch and comfortable fittingness of dip-formed article.

Tensile Strength (MPa)

Tensile strength was measured on the dumbbell specimen at a drawing rate of 500 mm/min by Tensilon tensile tester (the same as mentioned above) immediately before breaking.

Elongation at Break (%)

Elongation at break was measured on the dumbbell specimen at a drawing rate of 500 mm/min by Tensilon tensile tester (the same as mentioned above) immediately before breaking.

Tensile Stress Retention (%)

Tensile stress was measured on the dumbbell specimen by Tensilon tensile tester (the same as mentioned above). Tensile stress retention was determined from the tensile stress (Md0) as measured immediately after the elongation reached 100%, and the tensile stress (Md6) as measured when the specimen at the elongation of 100% was kept as it was for 6 minutes. The tensile stress retention (%) was defined as the ratio (%) of Md0/Md6×100. The larger the tensile stress retention, the more excellent the retention of close fittingness of dip-formed article.

Swelling Degree in Methyl Ethyl Ketone (MEK) (%)

A disc specimen having a diameter (D1) of 2 cm was punched out from a dip-formed article. The specimen was dipped in a MEK bath having a large volume at 20° C. for 72 hours, to be thereby swelled. Diameter (D2) was measured after swelling, and the swelling degree was calculated from the following equation (1).

$$\text{Swelling Degree in MEK (\%)} = (D2/D1)^2 \times 100 \quad (1)$$

Example 1

A pressure polymerization vessel was charged with 18 parts of acrylonitrile, 3 parts of methacrylic acid, 74 parts of 1,3-butadiene, 0.3 part of tert-dodecyl mercaptan as a molecular weight modifier, 150 parts of deionized water, 2.5 parts of sodium dodecylbenzenesulfonate, 0.2 part of potassium persulfate and 0.1 part of sodium ethylenediaminetetraacetate. Then the temperature of the content was elevated to 39° C. to initiate polymerization.

When the polymerization conversion of the total monomers added reached 60% (at this time, the polymerization conversion of acrylonitrile reached 66%), 4 parts of acrylonitrile and 1 part of methacrylic acid were added to a polymerization system. While the temperature was maintained at 39° C., the polymerization was continued until the polymerization conversion reached 95%. Thereafter 0.1 part of diethylhydroxlamine was added to terminate the polymerization.

Unreacted monomers were distilled off from the thus-prepared copolymer latex, and then, the solid content and pH value of the latex were adjusted to give a copolymer latex A having a solid content of 45% and a pH value of 8.5.

An aqueous dispersion of a vulcanizing agent was prepared by mixing together 3.5 parts of sulfur, 0.1 part of zinc oxide, 2 parts of zinc dibutylcarbamate, 0.03 part of potassium hydroxide and 5.63 parts of water. 11.26 parts of the aqueous dispersion of a vulcanizing agent was mixed with 250 parts of the above-mentioned copolymer latex (solid content: 100 parts), and then, deionized water was added to the mixture to prepare a dip-forming composition having a solid content of 30%.

An aqueous coagulant solution was prepared by mixing together 20 parts of calcium nitrate, 0.05 part of polyoxyethyleneoctyl phenyl ether (nonionic emulsifier) and 80 parts of water. A dip-forming glove form was dipped in the aqueous coagulant solution for 1 minute, and then, the glove form was taken out and dried at 50° C. for 3 minutes whereby the coagulant was deposited on the glove form.

The glove form having the coagulant deposited thereon was dipped in the above-mentioned dip-forming composition for 6 minutes. The glove form was taken out from the dip-forming composition, and then, the glove form having thereon a dip-formed layer was dried at 25° C. for 3 minutes and then dipped in warm water at 40° C. for 3 minutes to remove water-soluble impurities. Then the glove form was dried at 80° C. for 20 minutes and subsequently heat-treated at 120° C. for 25 minutes whereby the dip-formed layer was vulcanized. Finally the vulcanized, dip-formed layer was peeled from the glove form to obtain a dip-formed article of a glove shape. Properties of the dip-formed article were evaluated. The results are shown in Table 1.

Examples 2 and 3

Copolymer latexes B and C were prepared by the same procedures as described in Example 1 except that the amount of the initial monomer mixture charged, the amounts of acrylonitrile and methacrylic acid added after the initiation of polymerization, and the conditions under which the additional monomers were added were varied as shown in Table 1.

Dip-formed articles were made by the same procedures as described in Example 1 except that copolymer latexes B and C were used instead of copolymer latex A. Properties of the dip-formed article were evaluated. The results are shown in Table 1.

Comparative Examples 1 and 2

Copolymer latexes D and E were prepared by the same procedures as described in Example 1 except that the amount of the initial monomer mixture charged, the amounts of acrylonitrile and methacrylic acid added after the initiation of polymerization, and the conditions under which the additional monomers were added were varied as shown in Table 1.

Dip-formed articles were made by the same procedures as described in Example 1 except that copolymer latexes D and E were used instead of copolymer latex A. Properties of the dip-formed article were evaluated. The results are shown in Table 1.

TABLE 1

|  |  | Example | | | Comparative Example | |
|---|---|---|---|---|---|---|
|  |  | 1 | 2 | 3 | 1 | 2 |
| Monomer Composition (parts) | | | | | | |
| Initial charge: | 1,3-butadiene | 74 | 74 | 73 | 74 | 74 |
|  | Methacrylic acid (MA) | 3 | 3 | 2 | 4 | — |
|  | Acrylonitrile (AN) | 18 | 15 | 20 | 22 | 18 |
| % of initially charged MA to total MA | | 75 | 75 | 66.7 | 100 | 0 |
| % of initially charged AN to total AN | | 81.8 | 68.1 | 83.3 | 100 | 81.8 |
| Amount of AN added after initiation of polymerization *1 | | | | | | |
| at polymerization conversion of 40% | | — | 3.5(48%) | — | — | — |
| at polymerization conversion of 60% | | 4(66%) | — | 4(64%) | — | 4(67%) |
| at polymerization conversion of 70% | | — | 3.5(73%) | — | — | — |

TABLE 1-continued

| | Example | | | Comparative Example | |
|---|---|---|---|---|---|
| | 1 | 2 | 3 | 1 | 2 |
| Amount of MA added after initiation of polymerization | | | | | |
| at polymerization conversion of 40% | — | 1 | — | — | — |
| at polymerization conversion of 60% | 1 | — | 1 | — | 4 |
| Copolymer Latex | A | B | C | D | E |
| Properties of Dip-Formed Article | | | | | |
| Tensile stress at 300% elongation (MPa) | 1.9 | 1.8 | 2 | 2.5 | 3.5 |
| Tensile strength (MPa) | 23.5 | 25.2 | 24.8 | 16.7 | 17.8 |
| Elongation at break (%) | 610 | 630 | 610 | 570 | 510 |
| Retention of tensile stress (%) | 75 | 76 | 73 | 67 | 56 |
| Swelling degree in MEK (%) | 144 | 135 | 156 | 222 | 234 |

*1: Percents within parentheses indicate polymerization conversion of AN at which AN was added The following will be seen from Table 1.

The dip-formed article (Comparative Example 1) made from copolymer latex D prepared by copolymerization of the monomers, the total of which were initially charged, exhibited moderately good retention of tensile stress, but had slightly poor softness of touch, and slightly poor tensile strength.

The dip-formed article (Comparative Example 2) made from copolymer latex E prepared by copolymerization of the monomers wherein acrylonitrile and methacrylic acid were added in the midst of polymerization, but methacrylic acid was not initially charged, had a tensile strength of approximately the same magnitude as, but exhibited poor retention of tensile stress and poor softness of touch as compared with that of Comparative Example 1.

In contrast to the comparative examples, dip-formed articles (Examples 1-3) made from copolymer latexes A, B and C prepared by copolymerization of the monomers wherein part of acrylonitrile and part of methacrylic acid were initially charged and the remainders thereof were added in the midst of polymerization, exhibited good softness of touch, high tensile strength and high retention of tensile stress.

Example 4

A pressure polymerization vessel was charged with 23 parts of acrylonitrile, 3 parts of methacrylic acid, 73 parts of 1,3-butadiene, 0.3 part of tert-dodecyl mercaptan as a molecular weight modifier, 150 parts of deionized water, 2.5 parts of sodium dodecylbenzenesulfonate, 0.2 part of potassium persulfate and 0.1 part of sodium ethylenediaminetetraacetate. Then the temperature of the content was elevated to 37° C. to initiate polymerization.

When the polymerization conversion of the total monomers added reached 60%, 0.1 part of tert-dodecyl mercaptan and 1 part of methacrylic acid were added to a polymerization system. The temperature was elevated to 40° C., and, while the temperature was maintained at 40° C., the polymerization was continued until the polymerization conversion reached 97%. Thereafter 0.1 part of diethylhydroxlamine was added to terminate the polymerization.

Unreacted monomers were distilled off from the thus-prepared copolymer latex, and then, the solid content and pH value of the latex were adjusted to give a copolymer latex F having a solid content of 40% and a pH value of 8.5.

An aqueous dispersion of a vulcanizing agent was prepared by mixing together 3 parts of sulfur, 0.3 part of zinc oxide, 1.5 parts of zinc dibutylcarbamate, 1.5 parts of zinc diethylcarbamate, 0.03 part of potassium hydroxide and 6.33 parts of water. 12.66 parts of the aqueous dispersion of a vulcanizing agent was mixed with 250 parts of the above-mentioned copolymer latex (solid content: 100 parts), and then, deionized water was added to the mixture to prepare a dip-forming composition having a solid content of 30%.

An aqueous coagulant solution was prepared by mixing together 20 parts of calcium nitrate, 0.05 part of polyoxy-ethyleneoctyl phenyl ether (nonionic emulsifier) and 80 parts of water. A dip-forming glove form was dipped in the aqueous coagulant solution for 1 minute, and then, the glove form was taken out and dried at 50° C. for 3 minutes whereby the coagulant was deposited on the glove form.

The glove form having the coagulant deposited thereon was dipped in the above-mentioned dip-forming composition for 6 minutes. The glove form was taken out from the dip-forming composition, and then, the glove form having thereon a dip-formed layer was dried at 25° C. for 3 minutes and then dipped in warm water at 40° C. for 3 minutes to remove water-soluble impurities. Then the glove form was dried at 80° C. for 20 minutes and subsequently heat-treated at 120° C. for 25 minutes whereby the dip-formed layer was vulcanized. Finally the vulcanized, dip-formed layer was peeled from the glove form to obtain a dip-formed article of a glove shape. Properties of the dip-formed article were evaluated. The results are shown in Table 2.

Example 5

Copolymer latex G was prepared by the same procedures as described in Example 4 except that the composition of the initial monomer mixture charged, and the amount of methacrylic acid added after the initiation of polymerization were varied as shown in Table 2.

A dip-formed article was made by the same procedures as described in Example 4 except that copolymer latex G was used instead of copolymer latex F. Properties of the dip-formed article were evaluated. The results are shown in Table 2.

Comparative Example 3

Copolymer latex H was prepared by the same procedures as described in Example 4 except that the composition of the initial monomer mixture charged was varied as shown in Table 2 and methacrylic acid was not added after the initiation of polymerization.

A dip-formed article was made by the same procedures as described in Example 4 except that copolymer latex H was used instead of copolymer latex F. Properties of the dip-formed article were evaluated. The results are shown in Table 2.

Comparative Example 4

Copolymer latex J was prepared by the same procedures as described in Example 4 except that the composition of the initial monomer mixture charged and the amount of methacrylic acid added after the initiation of polymerization were varied as shown in Table 2.

A dip-formed article was made by the same procedures as described in Example 4 except that copolymer latex J was used instead of copolymer latex F. Properties of the dip-formed article were evaluated. The results are shown in Table 2.

TABLE 2

|  | Example | | Comparative Example | |
|---|---|---|---|---|
|  | 4 | 5 | 3 | 4 |
| Monomer Composition (parts) | | | | |
| Initial charge: 1,3-butadiene | 73 | 71 | 73 | 73 |
| Acrylonitrile (AN) | 23 | 26 | 23 | 23 |
| Methacrylic acid (MA) | 3 | 2 | 4 | — |
| % of initially charged MA to total MA | 75 | 67 | 100 | 0 |
| Amount of MA added after initiation of polymerization | 1 | 1 | — | 4 |
| Copolymer Latex | F | G | H | J |
| Properties of Dip-Formed Article | | | | |
| Tensile stress at 300% elongation (MPa) | 2.0 | 2.1 | 2.3 | 3.2 |
| Tensile strength (MPa) | 22.3 | 24.1 | 16.5 | 15.4 |
| Elongation at break (%) | 600 | 610 | 590 | 510 |

The following will be seen from Table 2.

The dip-formed article (Comparative Example 3) made from copolymer latex H prepared by copolymerization of the monomers, wherein methacrylic acid was not added after initiation of polymerization, exhibited moderately good softness of touch, but had poor tensile strength.

The dip-formed article (Comparative Example 4) made from copolymer latex J prepared by copolymerization of the monomers wherein methacrylic acid was not incorporated in the monomer mixture initially charged, exhibited poor softness of touch and poor tensile strength.

In contrast to the comparative examples, dip-formed articles (Examples 4 and 5) made from copolymer latexes F and G prepared by copolymerization of the monomers wherein part of methacrylic acid was initially charged and the remainder thereof was added in the midst of polymerization, exhibited good softness of touch and high tensile strength.

INDUSTRIAL APPLICABILITY

The dip-formed article of the present invention exhibits good softness of touch and comfortable fittingness, has high tensile strength and preferably exhibits high retention of close fittingness. This dip-formed article can have a thickness of about 0.1 mm to about 3 mm. Especially a thin dip-formed article having a thickness of 0.1 to 0.3 mm can be made.

Thus the dip-formed article of the present invention having the above characteristics is suitable for, for example, a nipple of nursing bottle, medical articles such as a dropper, a duct and a water pillow; toys such as a balloon, dolls and a ball, and sporting goods such as a ball; industrial articles such as a pressure molding bag and a gas storage bag; unsupported gloves and supported gloves for surgical, household, agricultural, fishery and industrial uses; and a finger cot. The dip-formed article is especially advantageously used as thin gloves such as thin surgical gloves.

The invention claimed is:

1. A process for making a dip-forming latex which comprises the steps of:
    copolymerizing 50 to 89.5 parts by weight of a conjugated diene monomer, 10 to 40 parts by weight of an ethylenically unsaturated nitrile monomer, 0.5 to 10 parts by weight of an ethylenically unsaturated acid monomer and 0 to 20 parts by weight of other copolymerizable ethylenicahy unsaturated monomer, provided that the total of these monomers is 100 parts by weight, by
    initiating said copolymerization with a monomer mixture comprising at least 90% by weight of the amount of conjugated diene monomer used, 55 to 85% by weight of the amount of ethylenically unsaturated nitrile monomer used, 50 to 85% by weight of the amount of ethylenically unsaturated acid monomer used and at least 90% by weight of the amount of other copolymerizable ethylenically unsaturated monomer used, and thereafter,
    adding the remainder of ethylenically unsaturated nitrile monomer while the polymerization conversion of the ethylenically unsaturated nitrile monomer is within a range of 40 to 95%,
    adding the remainder of ethylenicatly unsaturated acid monomer while the polymerization conversion of the total monomers added is within a range of 20 to 80%, and
    adding the remainders of conjugated diene monomer and other copolymerizable ethylenically unsaturated monomer at any time before the termination of copolymerization, to continue copolymerization.

2. The process for making a dip-forming latex according to claim 1, wherein said copolymerization is carried out by copolymerizing 55 to 84 parts by weight of a conjugated diene monomer, 15 to 36 parts by weight of an ethylenically unsaturated nitrile monomer, 1 to 9 parts by weight of an ethylenically unsaturated acid monomer and 0 to 15 parts by weight of other copolymerizable ethylenically unsaturated monomer, provided that the total of these monomers is 100 parts by weight.

3. The process for making a dip-forming latex according to claim 1, wherein said copolymerization is carried out by copolymerizing 65 to 81 parts by weight of a conjugated diene monomer, 18 to 27 parts by weight of an ethylenically unsaturated nitrile monomer, 1 to 8 parts by weight of an ethylenically unsaturated acid monomer and 0 to 10 parts by weight of other copolymerizable ethylenically unsaturated monomer, provided that the total of these monomers is 100 parts by weight.

4. The process for making a dip-forming latex according to claim 1, wherein, after the copolymerization of the monomer mixture is initiated, the remainder off ethylenically unsaturated nitrile monomer is added at two or more times.

5. The process for making a dip-forming latex according to claim 1, wherein the conjugated diene monomer is at least one monomer selected from the group consisting of 1,3-butadiene and isoprene.

6. The process for making a dip-forming latex according to claim 1, wherein the ethylenically unsaturated nitrile monomer is at least one monomer selected from the group consisting of acrylonitrile and methacrylonitrile.

7. The process for making a dip-forming latex according to claim 1, wherein the ethylenically unsaturated acid monomer is at least one monomer selected from the group consisting of ethylenically unsaturated carboxylic acid monomers.

* * * * *